US009506896B2

(12) United States Patent
Hwang et al.

(10) Patent No.: US 9,506,896 B2
(45) Date of Patent: Nov. 29, 2016

(54) METHOD AND APPARATUS FOR DETECTING AN ENVELOPE FOR ULTRASONIC SIGNALS

(71) Applicant: INDUSTRY-ACADEMIC COOPERATION FOUNDATION, YONSEI UNIVERSITY, Seoul (KR)

(72) Inventors: Do Sik Hwang, Seoul (KR); Jin Seong Jang, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 32 days.

(21) Appl. No.: 14/529,458

(22) Filed: Oct. 31, 2014

(65) Prior Publication Data

US 2015/0135838 A1     May 21, 2015

(30) Foreign Application Priority Data

Nov. 21, 2013   (KR) .......................... 10-2013-0141820

(51) Int. Cl.
| | |
|---|---|
| *G01N 9/24* | (2006.01) |
| *G01N 29/36* | (2006.01) |
| *G01N 29/06* | (2006.01) |
| *G01N 29/07* | (2006.01) |
| *G01N 29/44* | (2006.01) |

(52) U.S. Cl.
CPC .......... *G01N 29/36* (2013.01); *G01N 29/0654* (2013.01); *G01N 29/07* (2013.01); *G01N 29/4454* (2013.01)

(58) Field of Classification Search
CPC .............................. G01N 29/36; G01N 29/44
See application file for complete search history.

(56) References Cited

U.S. PATENT DOCUMENTS

| | | | | | |
|---|---|---|---|---|---|
| 4,276,802 | A | * | 7/1981 | Mieda | ...................... G10H 1/12 84/700 |
| 5,336,902 | A | * | 8/1994 | Nigaki | ...................... H01J 1/34 257/10 |

(Continued)

FOREIGN PATENT DOCUMENTS

| | | |
|---|---|---|
| JP | 2007195662 A | 8/2007 |
| JP | 2009-112625 A | 5/2009 |

(Continued)

OTHER PUBLICATIONS

Jin Ho Chang, et al; "A Novel Envelope Detector for High-Frame Rate, High-Frequency Ultrasound Imaging", IEEE Transactions on Ultrasonics, Ferroelectrics, and Frequency Control, vol. 54, No. 9, Sep. 2007, pp. 1792-1801.

(Continued)

*Primary Examiner* — Laura Martin
*Assistant Examiner* — Samir M Shah
(74) *Attorney, Agent, or Firm* — Ladas & Parry LLP (57) ABSTRACT

A method and apparatus for envelope detection are disclosed. An envelope detection method according to an embodiment of the invention can include: receiving ultrasonic signals reflected off a target object; detecting peaks by using differences in pulses in the received signals; and generating an envelope by connecting the detected peaks with straight or curved lines.

3 Claims, 6 Drawing Sheets

(56) References Cited

U.S. PATENT DOCUMENTS

| | | | | |
|---|---|---|---|---|
| 5,705,750 | A * | 1/1998 | Mizukami | G01F 23/2962 222/420 |
| 6,549,884 | B1 * | 4/2003 | Laroche | G10L 21/003 704/203 |
| 8,073,688 | B2 * | 12/2011 | Yoshioka | G10L 13/033 704/225 |
| 8,352,250 | B2 * | 1/2013 | Vos | G10L 21/02 704/200 |
| 9,082,416 | B2 * | 7/2015 | Krishnan | G10L 25/90 |
| 2003/0009336 | A1 * | 1/2003 | Kenmochi | G10L 13/07 704/258 |
| 2003/0221542 | A1 * | 12/2003 | Kenmochi | G10H 7/002 84/616 |
| 2006/0004569 | A1 * | 1/2006 | Yoshioka | G10L 13/033 704/225 |
| 2007/0261540 | A1 * | 11/2007 | Gremo | G10H 1/344 84/743 |
| 2010/0265800 | A1 * | 10/2010 | Eatwell | G01S 5/186 367/127 |

FOREIGN PATENT DOCUMENTS

| | | |
|---|---|---|
| JP | 2010-026323 A | 2/2010 |
| KR | 20110110408 A | 10/2011 |

OTHER PUBLICATIONS

Malene Schlaikjer, et al; "Trade Off Study on Different Envelope Detectors for B-mode Imaging", Published in: Ultrasonics, 2003 IEEE Symposium on (vol. 2); Oct. 5-8, 2003, pp. 1938-1941.

* cited by examiner

METHOD AND APPARATUS FOR DETECTING AN ENVELOPE FOR ULTRASONIC SIGNALS

CROSS-REFERENCE TO RELATED APPLICATIONS

This application claims the benefit of Korean Patent Application No. 10-2013-0141820, filed with the Korean Intellectual Property Office on Nov. 21, 2013, the disclosure of which is incorporated herein by reference in its entirety.

BACKGROUND

1. Technical Field

The present invention relates to a method and apparatus for detecting an envelope for ultrasonic signals.

2. Description of the Related Art

An ultrasonic B-mode image may be made by using high-frequency pulses with a wide frequency bandwidth. The emitted ultrasonic pulses may be reflected off an object in their original form and be inputted to a transducer.

The reflected signals may be composed of pulses continuing along the time axis, and a 2-dimensional imaging of these signals results in an image in which there are high-frequency components remaining. By detecting the envelope, it is possible to remove the high-frequency components and leave only the target of which imaging is desired.

In thus removing high-frequency components to image the target, the detection of the envelope is an essential procedure.

A technique for detecting the envelope by using the Hilbert Transform (Malene Schlaikjer, Jan P. Bagge, Ole M. Sorensen, and Jorgen Arendt Jensen, "Trade off study on different envelope detectors for B-mode imaging" Ultrasonics, 2003 IEEE Symposium) can provide ideal results, but the implementation method is complicated and may incur high costs and long computation times.

A technique employing in-phase quadrature demodulation (Jin Ho Chang, Jesse T. Yen, and K. Kirk Shung, "A Novel Envelope Detector for High-Frame Rate, High Frequency Ultrasound Imaging" IEEE Transactions on Ultrasonics, Ferroelectrics, and Frequency Control, vol. 54, no. 9, Sep. 2007) may involve choosing a center frequency, applying sine and cosine functions, and passing the results through a low-pass filter.

However, if the center frequency is not chosen correctly, the modulation may not be done accurately, and the detection of the envelope may not be properly achieved.

As such, there is a demand for a technique that enables not only accurate envelope detection but also a decrease in the time required for envelope detection.

In particular, since ultrasound diagnosis additionally requires the processing of various signals and images, there is a growing need for a technique that allows faster processing of ultrasonic data.

SUMMARY

An aspect of the invention is to propose a method and apparatus for detecting an envelope for ultrasonic signals that provide high accuracy while greatly reducing computation times.

One aspect of the invention provides an envelope detection method that can provide high accuracy while greatly reducing computation times.

An envelope detection method according to an embodiment of the invention can include: (a) receiving ultrasonic signals reflected off a target object; (b) detecting peaks by using differences in pulses in the received signals; and (c) generating an envelope by connecting the detected peaks with straight or curved lines.

An embodiment of the invention can further include an operation of performing an absolute value computation on the received signals, before step (b).

Step (b) can include detecting the peaks by using differences in absolute values according to time, where the absolute value at a point where the absolute value changes from an increasing trend to a decreasing trend can be determined to be a peak.

The curved lines can include quadric or cubic curves.

Another aspect of the invention provides an envelope detection apparatus that can provide high accuracy while greatly reducing computation times.

An envelope detection apparatus according to an embodiment of the invention can include: a receiving unit configured to receive ultrasonic signals reflected off a target object; a peak detection unit configured to detect peaks by using differences in pulses in the received signals; and an envelope detection unit configured to generate an envelope by connecting the detected peaks with straight or curved lines.

The envelope detection apparatus can further include a pre-processing unit that is configured to perform an absolute value computation on the received signals, where the peak detection unit can detect peaks by using differences in the absolute values converted by the pre-processing unit.

The peak detection unit can detect the peaks by using differences in absolute values according to time. Ultrasonic images really used in diagnosis comprise the absolute values of ultrasonic values.

With an envelope detection method and an envelope detection apparatus according to an embodiment of the invention, an envelope can be generated by detecting the peaks in the signals reflected off a target object, so that the accuracy of the envelope detection can be increased.

Also, with an embodiment of the invention, the envelope detection does not require filtering, so that the envelope can be detected based on accurate values.

Furthermore, since the envelope detection does not require filtering, the computation speed can be increased, and the quality of the images obtained can be improved.

Additional aspects and advantages of the present invention will be set forth in part in the description which follows, and in part will be obvious from the description, or may be learned by practice of the invention.

DETAILED DESCRIPTION

As the present invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed in the present invention. In describing the drawings, like reference numerals are used for like elements.

While such terms as "first" and "second," etc., may be used to describe various components, such components must not be limited to the above terms. The above terms are used only to distinguish one component from another.

The terms used in the present specification are merely used to describe particular embodiments, and are not intended to limit the present invention. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

The present invention relates to detecting an envelope by using differences in ultrasonic signals to detect peaks and connecting the detected peaks with lines or curves.

Certain embodiments of the invention will be described below in more detail with reference to the accompanying drawings.

Figure 1:
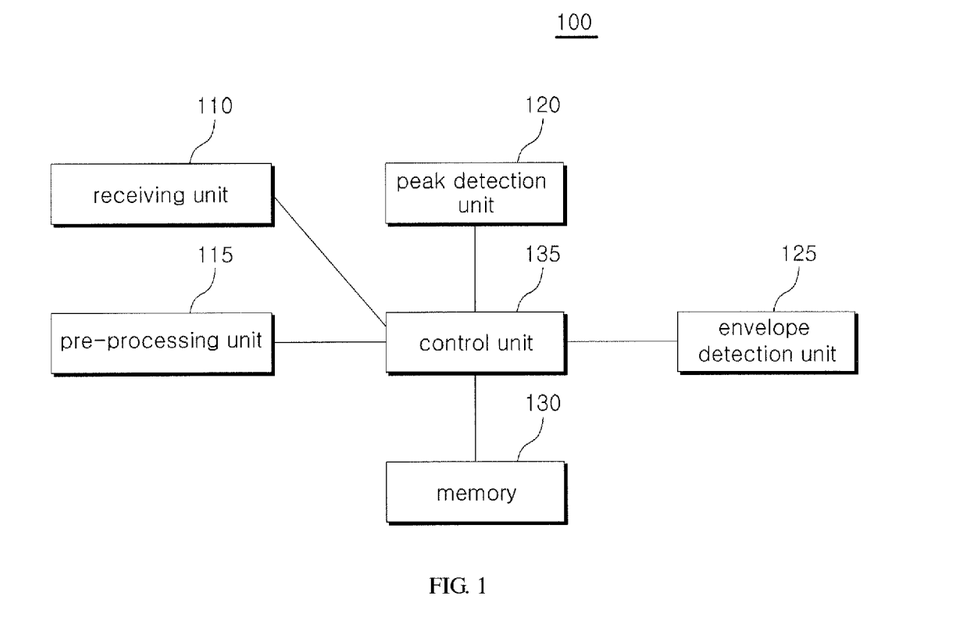
FIG. 1 schematically illustrates the internal composition of an envelope detection apparatus according to an embodiment of the invention.
Figure 2:
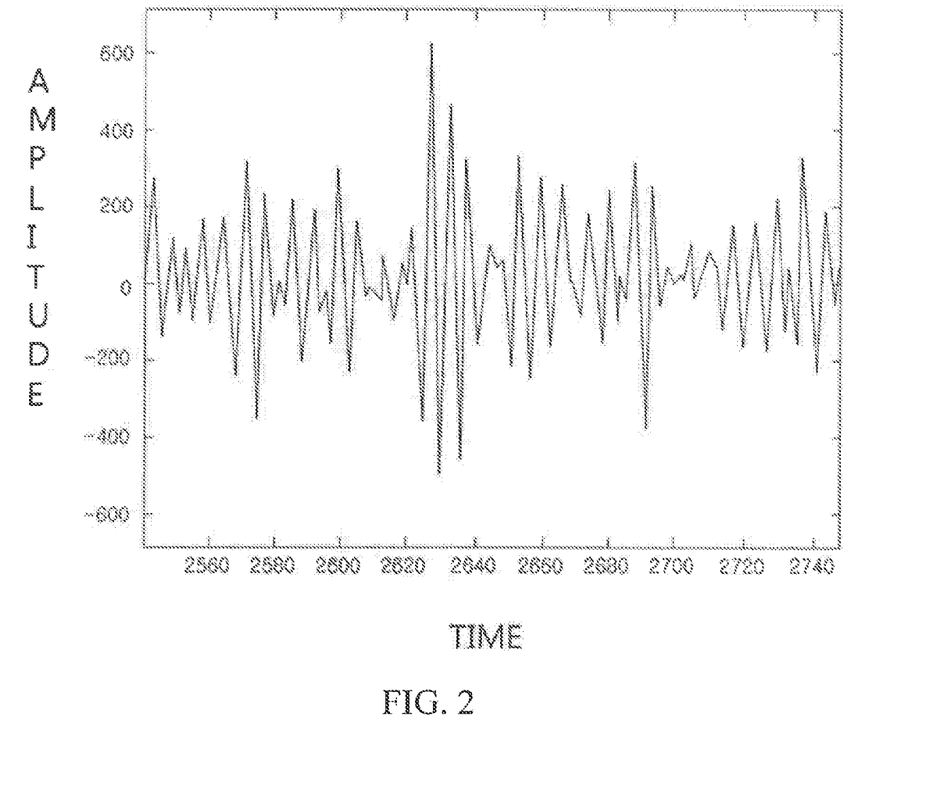
FIG. 2 shows an example of reflected ultrasonic waves according to an embodiment of the invention.
Figure 3:
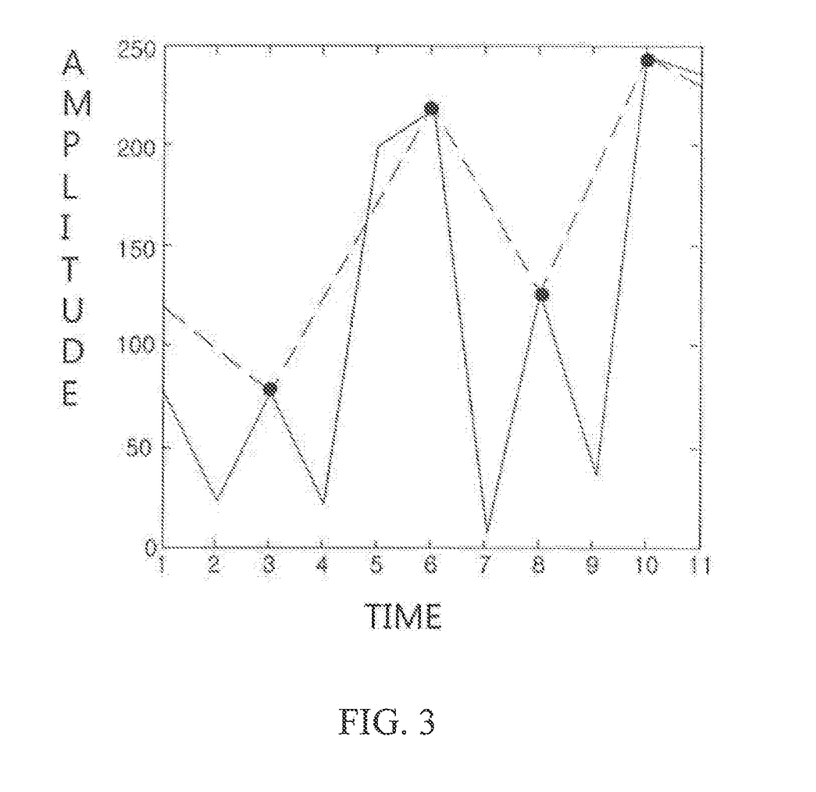
FIG. 3 illustrates an approach for the detection of peaks according to an embodiment of the invention.
Figure 4:
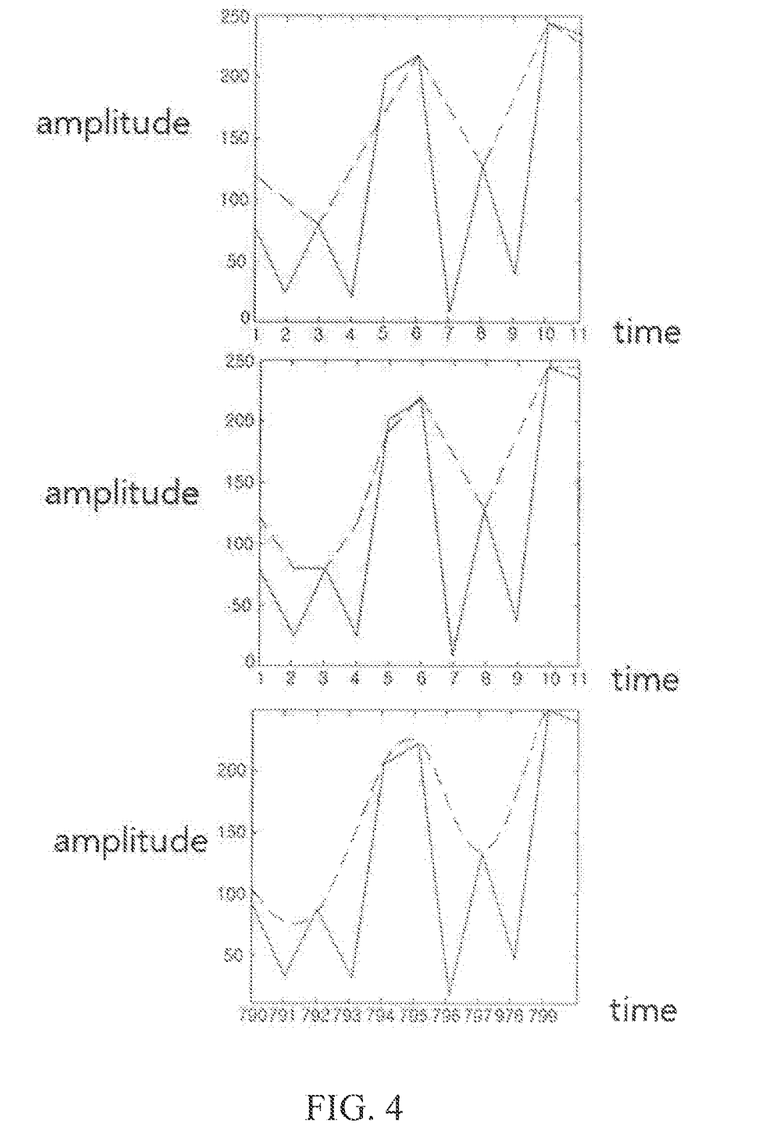
FIG. 4 illustrates approaches for connecting the peaks according to an embodiment of the invention.
Figure 5:
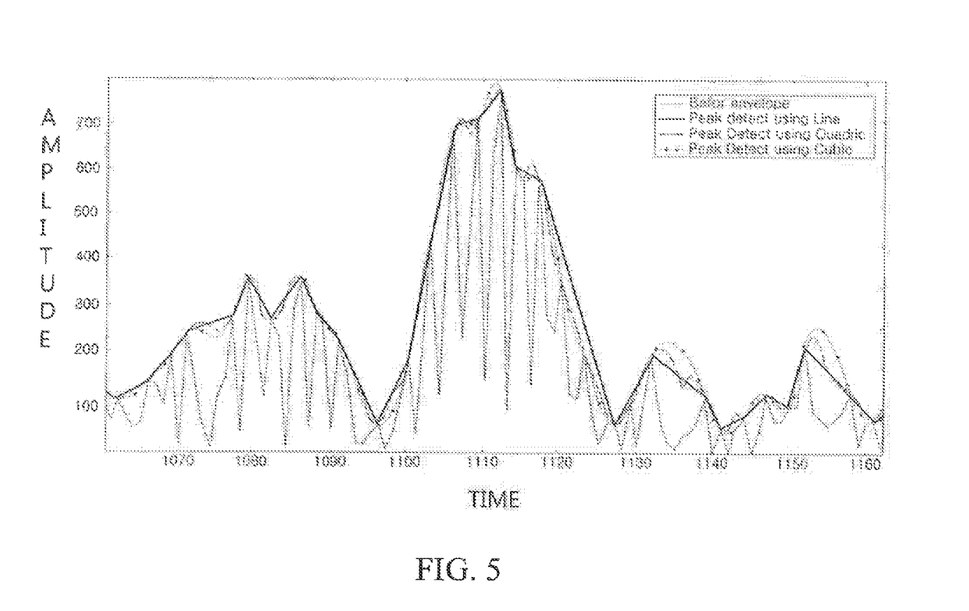
FIG. 5 shows examples of envelopes detected according to the type of peak connection according to an embodiment of the invention.
Figure 6:
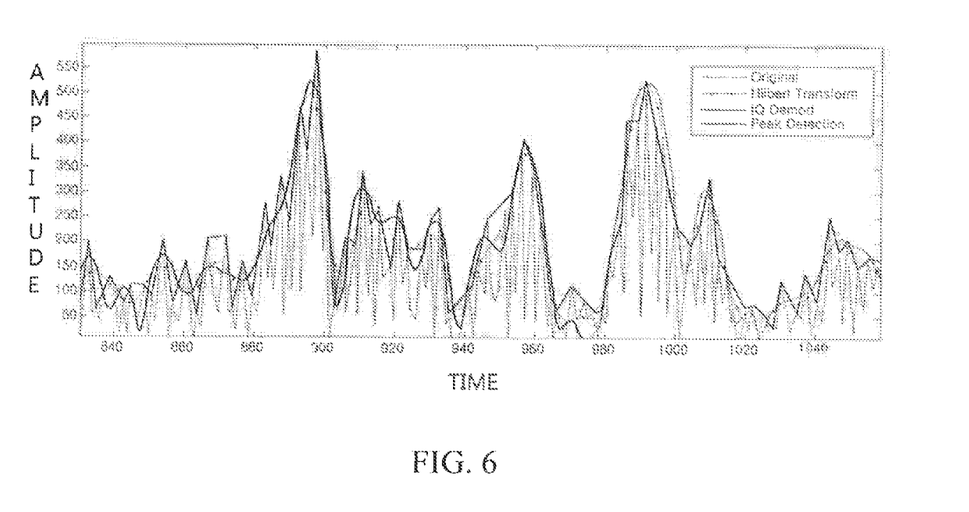
FIG. 6 compares envelopes detected according to the related art with an envelope detected according to an embodiment of the invention.

FIG. 1 schematically illustrates the internal composition of an envelope detection apparatus according to an embodiment of the invention, FIG. 2 shows an example of reflected ultrasonic waves according to an embodiment of the invention, FIG. 3 illustrates an approach for detecting peaks according to an embodiment of the invention, FIG. 4 illustrates approaches for connecting the peaks according to an embodiment of the invention, FIG. 5 shows examples of envelopes detected according to the type of peak connection according to an embodiment of the invention, and FIG. 6 compares envelopes detected according to the related art with an envelope detected according to an embodiment of the invention.

Referring to FIG. 1, an envelope detection apparatus 100 according to an embodiment of the invention may include a receiving unit 110, a pre-processing unit 115, a peak detection unit 120, an envelope detection unit 125, a memory 130, and a control unit 135.

The receiving unit 110 may serve to receive the ultrasonic signals that are emitted to and reflected from the target object.

The pre-processing unit 115 may serve to perform an absolute value computation on the ultrasonic signals received through the receiving unit 110.

As illustrated in FIG. 2, the reflected ultrasonic signals may continue along the time axis, with the pulses portraying both positive and negative values. When the pulses of the ultrasonic signals include both positive and negative values as in FIG. 2, it can be difficult to accurately detect the envelope.

Thus, the pre-processing unit 115 can be used to apply an absolute value computation on the pulses of the reflected ultrasonic signals and change all of the values into positive values, before performing the peak detection. Ultrasonic images really used in diagnosis comprise the absolute values of ultrasonic values.

Moreover, since an ultrasonic image may be generated with only positive values, it may be beneficial to perform an absolute value computation.

The peak detection unit 120 may serve to detect each of the peaks by using differences in the absolute values converted by the pre-processing unit 115.

For example, the peak detection unit 120 may use differences in the absolute values according to time, to determine the absolute values at points where an absolute value changes from an increasing trend and begins to decrease. That is, if the absolute values at time points t0, t1, and t2 are 1, 2, and 1, respectively, then the absolute value at point t1 may be determined to be a peak.

FIG. 3 illustrates peaks detected by the peak detection unit 120. The envelope detection unit 125 may serve to generate an envelope by connecting with lines or curves the peaks detected through the peak detection unit 120.

As illustrated in FIG. 4, the envelope detection unit 125 can connect the peaks detected by the peak detection unit 120 to generate the envelope in any one of a linear, quadric, and cubic form. FIG. 4 shows examples of envelope forms that can be obtained according to the method of connecting the peaks.

TABLE 1

| data length(samples) | IQ Demod. (related art) | Peak Detection (present invention) |
| --- | --- | --- |
| 1000 | 0.233 ms | 0.053 ms |
| 2000 | 0.437 ms | 0.103 ms |
| 3000 | 0.625 ms | 0.153 ms |

As shown in Table 1 above, an envelope generation method based on peak detection according to an embodiment of the invention can provide very fast computation times, as there are no delays and there is no filtering used.

FIG. 5 shows examples of envelopes detected according to the connection type. As in FIG. 5, it can be seen that, although there may be certain differences in detail between the envelopes according to connection type, the overall patterns of the envelopes are similar.

FIG. 6 shows examples of envelopes that were detected by methods according to the related and according to an embodiment of the invention. As shown in FIG. 6, an envelope detection method according to an embodiment of the invention does not require a filter and can therefore detect an envelope regardless of filter parameters (e.g. order, cut-off frequency) or a center frequency.

Also, as shown in FIG. 6, an embodiment of the invention can detect an envelope by using differences between minimum values and maximum values in the pulses after taking absolute values for the reflected signals, so that the envelope can be detected based on accurate values of the signals without filtering, with a very fast computation speed and no time delays.

The memory 130 may serve to store various algorithms required for operating an envelope detection apparatus 100 according to an embodiment of the invention, as well as various data (e.g. converted ultrasonic signals, peaks, detected envelopes, etc.) obtained during the envelope detection process, and the like.

The control unit 135 may serve to control the internal components (e.g. the receiving unit 110, pre-processing unit 115, peak detection unit 120, envelope detection unit 125, memory 130, etc.) of an envelope detection apparatus 100 according to an embodiment of the invention.

Figure 7:
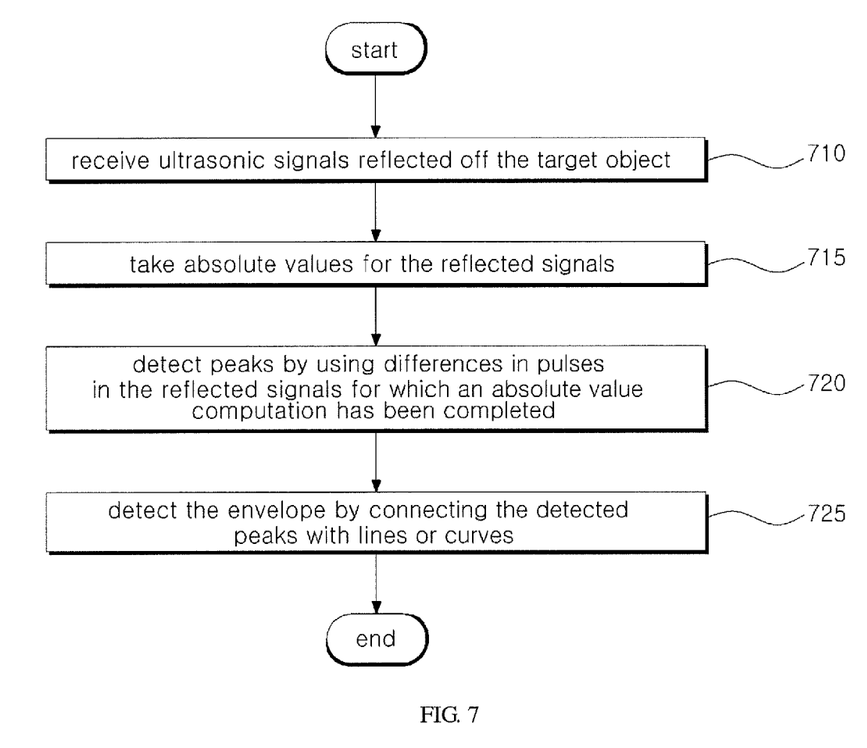
FIG. 7 is a flowchart illustrating an envelope detection method according to an embodiment of the invention.

FIG. 7 is a flowchart illustrating an envelope detection method according to an embodiment of the invention, and FIG. 8 compares an image obtained by using an envelope detected according to the related art with an image obtained by using an envelope detected according to an embodiment of the invention. The operations described below may be performed by an internal component of an envelope detection apparatus 100, but for convenience, the operations will be described as being performed by the envelope detection apparatus itself.

Also, the descriptions below will focus on the procedures of receiving the reflected signals and detecting an envelope, after the ultrasonic signals emitted from an ultrasound emission module are reflected off a target object.

In operation 710, the envelope detection apparatus 100 may receive the ultrasonic signals reflected off the target object. In the descriptions that follow, the reflected ultrasonic signals will be referred to as reflected signals for easier understanding and easier explanation.

As described above, the reflected signals that are reflected from the target object may take the form of a series of pulses that continue along the time axis. The pulses of the reflected signals may include both positive and negative values.

Thus, for the detection of peaks in the received reflected signals, the envelope detection apparatus 100 may perform an absolute value computation on the received reflected signals as a pre-processing operation (operation 715).

That is, the envelope detection apparatus 100 can change the negative values, from among the pulse values of the received reflected signals, into positive values.

In operation 720, the envelope detection apparatus 100 may detect peaks by using differences in the pulses of the reflected signals, for which an absolute value computation has been completed.

For example, the envelope detection apparatus 100 can determine the peaks from differences between minimum values and maximum values in the pulses of the reflected signals for which the absolute value computation has been completed.

In another example, the envelope detection apparatus can detect the peaks from differences between the minimum and maximum values in all pulses included in the respective time segments divided for certain time intervals.

In operation 725, the envelope detection apparatus 100 may detect the envelope by connecting the detected peaks with lines or curves.

As described above, the envelope detection apparatus 100 can detect the envelope by connecting the detected peaks with straight lines or curves.

FIG. 8 compares an image obtained by using an envelope detected according to the related art with an image obtained by using an envelope detected according to an embodiment of the invention. Numeral 810 indicates the original image, numeral 820 indicates an image obtained by primary modulation, and numeral 830 indicates an image obtained by envelope detection according to an embodiment of the invention.

As shown in FIG. 8, an envelope detection method according to an embodiment of the invention can greatly reduce the time required for obtaining an image based on envelope detection, since it does not employ methods such as filtering, and can also provide a higher image quality compared to conventional methods.

A method of detecting envelopes using ultrasonic signals according to an embodiment of the present invention can be implemented in the form of program instructions that may be performed using various computer means and can be recorded in a computer-readable medium. Such a computer-readable medium can include program instructions, data files, data structures, etc., alone or in combination.

The program instructions recorded on the medium can be designed and configured specifically for the present invention or can be a type of medium known to and used by the skilled person in the field of computer software. Examples of a computer-readable medium may include magnetic media such as hard disks, floppy disks, magnetic tapes, etc., optical media such as CD-ROM's, DVD's, etc., magneto-optical media such as floptical disks, etc., and hardware devices such as ROM, RAM, flash memory, etc. Examples of the program of instructions may include not only machine language codes produced by a compiler but also high-level language codes that can be executed by a computer through the use of an interpreter, etc. The hardware mentioned above can be made to operate as one or more software modules that perform the actions of the embodiments of the invention, and vice versa.

While the present invention has been described above using particular examples, including specific elements, by way of limited embodiments and drawings, it is to be appreciated that these are provided merely to aid the overall understanding of the present invention, the present invention is not to be limited to the embodiments above, and various modifications and alterations can be made from the disclosures above by a person having ordinary skill in the technical field to which the present invention pertains.

What is claimed is:

1. An envelope detection method for generating ultrasonic images comprising:
   receiving ultrasonic signals reflected off a target object;
   performing an absolute vale computation on the received signal;
   detecting peaks by using differences in amplitudes of absolute values according to time in the received signals; and
   generating an envelope by connecting the detected peaks with straight or curved lines,
   wherein the detecting peaks step comprises determining an amplitude of an absolute value at a point where the amplitude of the absolute value changes from an increasing trend to a decreasing trend to be a peak.

2. The envelope detection method of claim 1, wherein the curved lines are quadratic or cubic curves.

3. An envelope detection apparatus for generating ultrasonic images comprising:
   a receiving unit configured to receive ultrasonic signals reflected off a target object;
   a pre-processing unit configured to perform an absolute value computation on the received signals;
   a peak detection unit configured to detect peaks by using differences in amplitudes of absolute values according to time; and
   an envelope detection unit configured to generate an envelope by connecting the detected peaks with straight or curved lines,
   wherein the peak detection unit determines an amplitude of an absolute value at a point where the amplitude of the absolute value change from an increasing trend to a decreasing trend to be a peek.

\* \* \* \* \*